(12) United States Patent
Reglat et al.

(10) Patent No.: US 6,343,501 B1
(45) Date of Patent: Feb. 5, 2002

(54) SYSTEM AND METHOD FOR DETERMINING THE PROCESS VISCOSITY OF A FLUID IN A FILM METERING DEVICE

(75) Inventors: Olivier Reglat; Philippe A. Tanguy, both of Montreal (CA)

(73) Assignee: Polyvalor S.E.C. (CA)

( * ) Notice: Subject to any disclaimer, the term of this patent is extended or adjusted under 35 U.S.C. 154(b) by 0 days.

(21) Appl. No.: 09/520,875

(22) Filed: Mar. 8, 2000

(51) Int. Cl.$^7$ .............................. B05C 1/06; B05D 1/28; G01N 11/00; G01N 11/04
(52) U.S. Cl. .................... 73/54.01; 73/54.02; 73/53.03; 118/712; 118/665; 427/8; 427/211
(58) Field of Search ............................. 73/54.01, 54.02, 73/53.03, 159; 118/712, 414, 117, 424, 665, 667; 427/8, 149, 211, 411

(56) References Cited

U.S. PATENT DOCUMENTS

| | | | | |
|---|---|---|---|---|
| 3,110,172 A | * | 11/1963 | Irwin | 73/54 |
| 3,785,196 A | * | 1/1974 | Smith | 73/64 |
| 4,466,274 A | * | 8/1984 | Starr, Jr. | 73/54 |
| 4,895,019 A | * | 1/1990 | Lehmikangas et al. | 73/63 |
| 5,145,525 A | * | 9/1992 | Fromm et al. | 118/260 |
| 5,212,981 A | * | 5/1993 | Laun et al. | 73/54.01 |
| 5,413,806 A | * | 5/1995 | Braun | 427/9 |
| 5,457,987 A | * | 10/1995 | Bulou et al. | 73/64.49 |
| 5,590,560 A | * | 1/1997 | Joos et al. | 73/64.48 |
| 5,759,279 A | | 6/1998 | Reglat et al. | 118/681 |
| 5,902,401 A | | 5/1999 | Elvidge et al. | 118/262 |
| 5,937,258 A | * | 8/1999 | Acquaviva et al. | 399/341 |
| 5,996,404 A | * | 12/1999 | McCue et al. | 73/54.01 |
| 6,098,450 A | * | 8/2000 | Willenbacher et al. | 73/54.01 |

OTHER PUBLICATIONS

Olivier Réglat and Philippe A. Tanguy, Rheological investigations of $CaCO_3$ slurries in the metering nip of a metering size press, Tappi Journal, vol. 81, No. 5, 1997, Canada.

O. Réglat and P.A. Tanguy, Experimental Study of the Flow in the Metering Nip of a Metering–Size Press, AIChE Journal, vol. 43, No. 11, Nov., 1997, Canada.

* cited by examiner

Primary Examiner—Hezron Williams
Assistant Examiner—David J. Wiggins
(74) Attorney, Agent, or Firm—Bourque & Associates, PA

(57) ABSTRACT

The system and the method are used to determine the process viscosity ($\mu$) of a fluid (22) in a film metering device (10) used to form a film (24) to be applied on a substrate (20), such as a paper web or any other suitable flexible materials. The apparent shear rate ($\dot{\gamma}$) of the fluid, indicative of the flow field, may also be calculated. These parameters are calculated using a pressure profile representing the pressure of the fluid between a transfer roll (12) and a metering rod (30) which controls the thickness of the coating film (24). The torque (T) applied on the metering rod (30) is also measured and taken into account in the calculations. The system and method allow the process viscosity ($\mu$) to be easily and accurately determined during the operation of the film metering device (10) without the need of testing the fluid in an external device and attempting to extrapolate the results to the process.

20 Claims, 4 Drawing Sheets

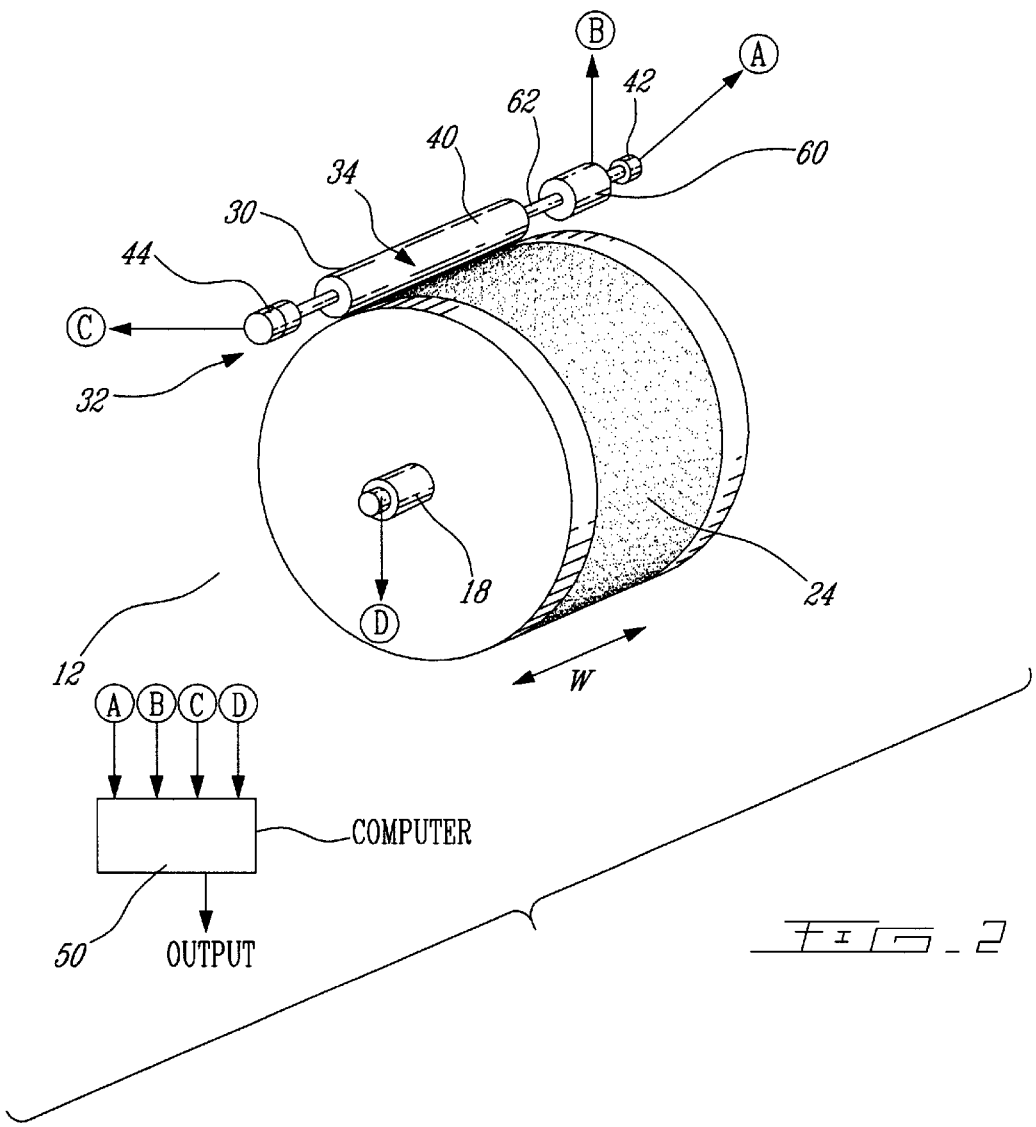
FIG_2

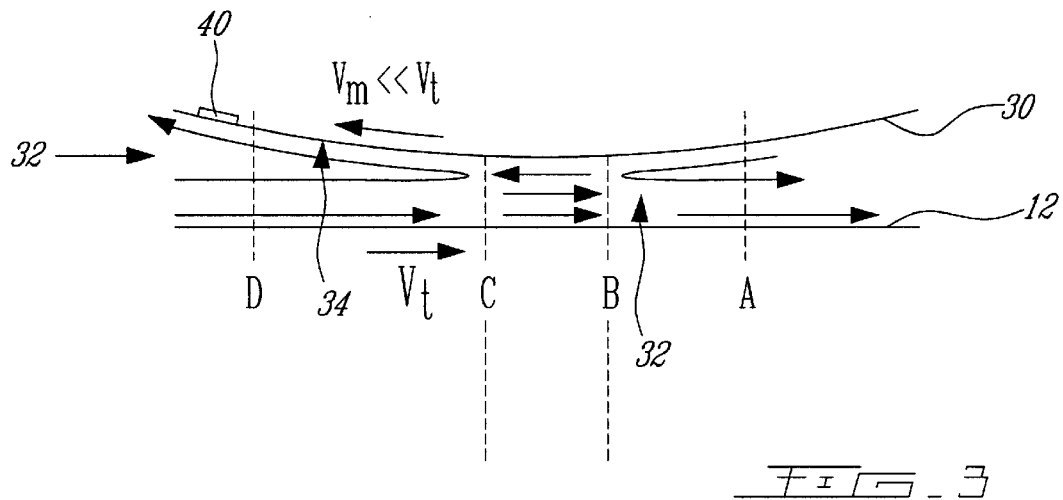
FIG_3
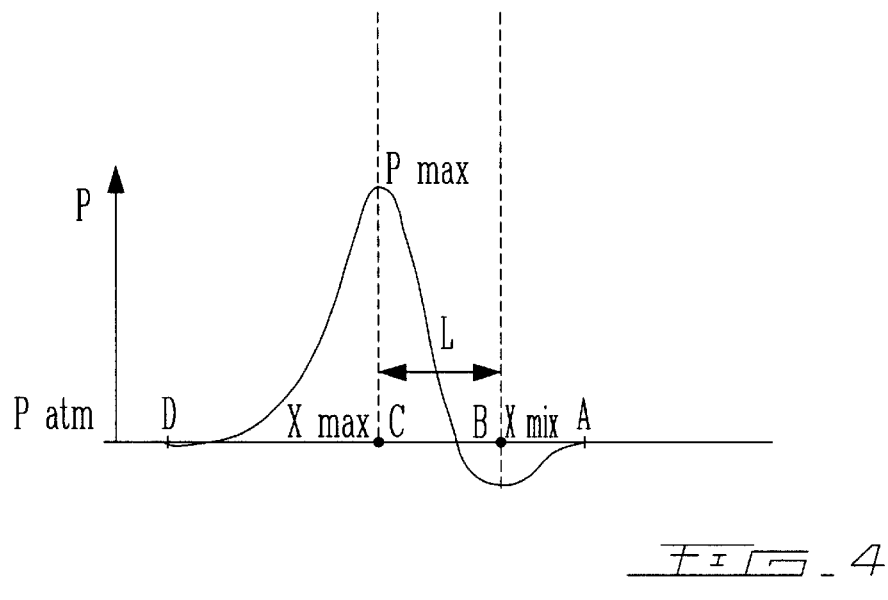
FIG_4

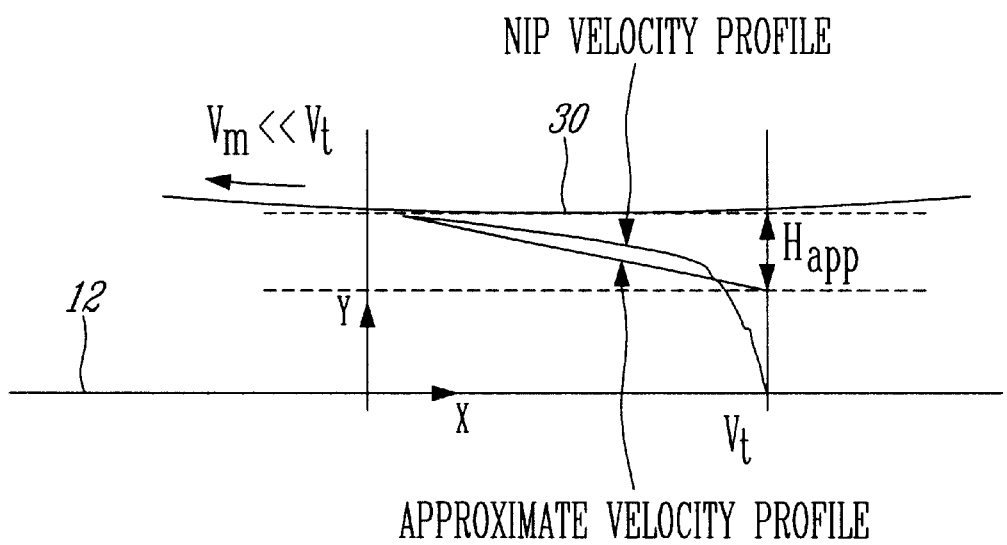
FIG_5

//SYSTEM AND METHOD FOR DETERMINING THE PROCESS VISCOSITY OF A FLUID IN A FILM METERING DEVICE

The present invention relates to a system and a method for determining the process viscosity ($\mu$) of a fluid in a film metering device. The process viscosity ($\mu$) is calculated using operating parameters and measurements made on the film metering device while it applies a coating layer on a substrate, such as a paper web or any other suitable flexible material. This invention allows the process viscosity ($\mu$) of the coating fluid to be continuously monitored.

The paper coating industry is one area where film metering devices are used. A common film metering device in that industry is the metering-size press, which has been found to be flexible in dealing with a wide range of coating fluids of various specific weights and kinds of paper webs. FIG. 1 shows a typical example of a metering-size press (10) as found in the prior art. It comprises a transfer roll (12) and a proximate backing roll (14), both having the same tangential speed but rotating in opposite directions. The tangential speed ($V_t$) of these rolls (12,14) is typically from 50 to 3000 m/min. The transfer roll (12) and the backing roll (14) are pushed one against the other with a preset load. The coating fluid (22) is carried between the rolls (12,14) and picked up by a paper web (20) wound around the backing roll (14). The paper web (20) picks up most of the coating fluid (22) adhering on the transfer roll (12) and forming a coating film (24).

The fluid (22) is supplied to the transfer roll (12) through a feeding chamber or box (26) having a transversal length (W) that substantially corresponds to that of the film (24). The thickness of the film (24) is controlled by means of a rigid metering rod (30), usually chrome-plated, rotating in the same direction than that of the transfer roll (12) but at a much lower tangential speed ($V_m$), typically 60 m/min or less. Its diameter is small compared to that of the transfer roll (12). The excess of coating fluid (22) is scraped off from both the metering rod (30) by a blade (not shown).

The metering roll (30) is pushed against the transfer roll (12) with a preset load. The presence of the coating fluid (22) creates a thin space between the transfer roll (12) and the metering rod (30), which space is referred to as the metering nip (32). The minimum gap in the metering nip (32) is in fact extremely small, of the order of 10 to 100 $\mu$m. Such small gap is difficult to obtain with a pair of hard rolls, especially on a full-size metering-size press (10) which can be up to 8 meters wide. In practice, the transfer roll (12) is usually covered with a soft elastomeric outer layer that reduces the risks of clashing with the metering rod (30) and allows more tolerance on the runout. The minimum gap results from an equilibrium between the deformation of the fluid and the elastic forces due to the deformation of the elastomeric outer layer. Nevertheless, the transfer roll (12) can also be provided with a rigid outer surface, such as a chrome-plated surface. The flow pattern in a metering nip is characterized by a deformation of the fluid, resulting from a combination of shear and extension. It is also characterized by a deformation rate that reaches very high values. For example, the deformation rate can be as high as $10^6$ s$^{-1}$ in a metering nip whose minimum gap is 20 $\mu$m and with a transfer roll having a tangential speed ($V_t$) of 2000 m/min.

The viscosity is a material function of a fluid. It is measured in well defined standard flow conditions. Two viscosities can be defined, according to the type of deformation imparted to the fluid, namely the shear viscosity and the elongational or extensional viscosity. The shear viscosity of a given fluid can be obtained using commercial rheometers, such as rotational rheometers with cone and plate geometries, rheometers with coaxial cylinders, or capillary rheometers. Measurements are done in well established permanent flow conditions or oscillatory flow conditions. Usually, corrections must be done to compensate end effects, wall effects or temperature effects. Unlikely, the extensional viscosity is usually difficult to measure since purely extensional flows cannot be easily generated. It is known from the theory that Newtonian fluids have an extensional viscosity which is three times the shear viscosity.

Real flows are generally quite different from standard flow conditions. In a process, a fluid is submitted to a combination of shear and extension that may vary in time. As a result, the viscosity of the fluid changes as well. The fluid behavior is more accurately characterized in terms of a process viscosity, which refers to the viscosity of a fluid in a given location of the process and under given operating conditions. The problem is that the only accurate way to measure the process viscosity is at the given location and under the real operating conditions. However, this has proved hitherto to be very difficult to achieve.

Although in-situ measurements of the behavior of the fluid were not possible, some techniques were devised to provide some ways of controlling the quality of the fluid to be used in a process. For instance, the Brookfield viscosity is measured with a spindle rotating at low speed in a small container filled with the fluid under investigation. There is also the Hercules viscosity, where the fluid is set between two concentric cylinders having non-identical rotation speeds. Measurements are made while the rotation speeds of the cylinder are continuously accelerating and decelerating. These two measurements may be used as reference values.

A concentrated suspension can be defined as liquids having a solid percentage of 30% or more by weight. The internal structure of concentrated suspensions varies depending on the flow conditions to which it is submitted. Moreover, they are memory fluids. Many examples in the scientific literature show that it is almost impossible to predict the behavior of a concentrated suspension in a metering nip by either a standard viscosity measurement or a viscosity evaluation other than an in-situ measurement.

The present invention is aimed at satisfying the need of being capable to accurately determine the process viscosity of a fluid in a film metering device and while the device is in use. The system and the method of the present invention allows the fluid to be monitored in a continuous manner, giving direct and immediate information about the process viscosity as well as the apparent shear rate of the fluid. More particularly, the present invention provides a method for determining the process viscosity ($\mu$) of a fluid supplied to a film metering device. The film metering device includes a transfer roll and a metering rod. A metering nip is formed between the transfer roll and the metering rod. The metering rod has an outer cylindrical surface and is disposed parallel to the transfer roll. The method comprises the steps of obtaining a pressure profile of the fluid, representing the pressure of the fluid in the metering nip on the surface of the metering rod; measuring a value of a torque (T) applied on the metering rod when the pressure profile is taken; determining a maximum pressure value ($P_{max}$) and a minimum pressure value ($P_{min}$) from the pressure profile and respective positions ($X_{max}$, $X_{min}$) thereof; determining a value of a circumferential spacing (L) between the position ($X_{max}$) of the maximum pressure value ($P_{max}$) and the position ($X_{min}$) of the minimum pressure value ($P_{min}$); and calculating the process viscosity ($\mu$) of the fluid using the values of the torque (T), the maximum pressure ($P_{max}$), the minimum pressure ($P_{min}$) and the circumferential spacing (L).

The present invention also provides a system for determining the process viscosity ($\mu$) of a fluid supplied to a film metering. The film metering device includes a transfer roll and a metering rod, both forming between them a metering nip. The metering rod has an outer cylindrical surface and is disposed parallel to the transfer roll. The system comprises first means for obtaining a pressure profile of the fluid representing the pressure of the fluid in the metering nip on the surface of the metering rod; second means for measuring a value of a torque (T) applied on the metering rod when the pressure profile is taken; third means for determining a maximum value ($P_{max}$) and a minimum value ($P_{min}$) from the pressure profile and relative positions ($X_{max}$, $X_{min}$) thereof; fourth means for determining the value of a circumferential spacing (L) between the position ($X_{max}$) of the maximum pressure ($P_{max}$) and the position ($X_{min}$) of the minimum pressure ($P_{min}$); and fifth means for calculating the process viscosity ($\mu$) of the fluid using the values of the torque (T), the maximum pressure value ($P_{max}$), the minimum pressure value ($P_{min}$) and the circumferential spacing (L).

The present invention also provides a system for determining the process viscosity ($\mu$) of a fluid supplied to a film metering device. The film metering device includes a transfer roll and an adjacently-disposed metering rod, both forming between them a metering nip. The metering rod has a cylindrical outer surface and a rotation speed ($\omega$). The system comprises a pressure sensor flush-mounted on the outer surface of the metering rod. The pressure sensor generates a first signal (P) indicative of the pressure thereon. A torque sensor is connected to the metering rod. The torque sensor generates a second signal (T) indicative of the torque applied on the metering rod. A computer is provided to record and process data. The computer calculates the process viscosity ($\mu$) based on the first signal (P), the second signal (T) and the rotation speed ($\omega$).

The present invention will be better understood from the following description and appended figures in which:

FIG. 2 is a partial perspective view of a metering device provided with a system according to the present invention.

FIG. 3 is a schematic side view of a typical flow pattern of the coating fluid in the metering nip.

FIG. 4 is a graph showing an example of a pressure profile representing the surface pressure distribution on the metering rod of FIG. 3.

FIG. 5 is a schematic representation of the velocity profile in the metering nip.

Figure 1:
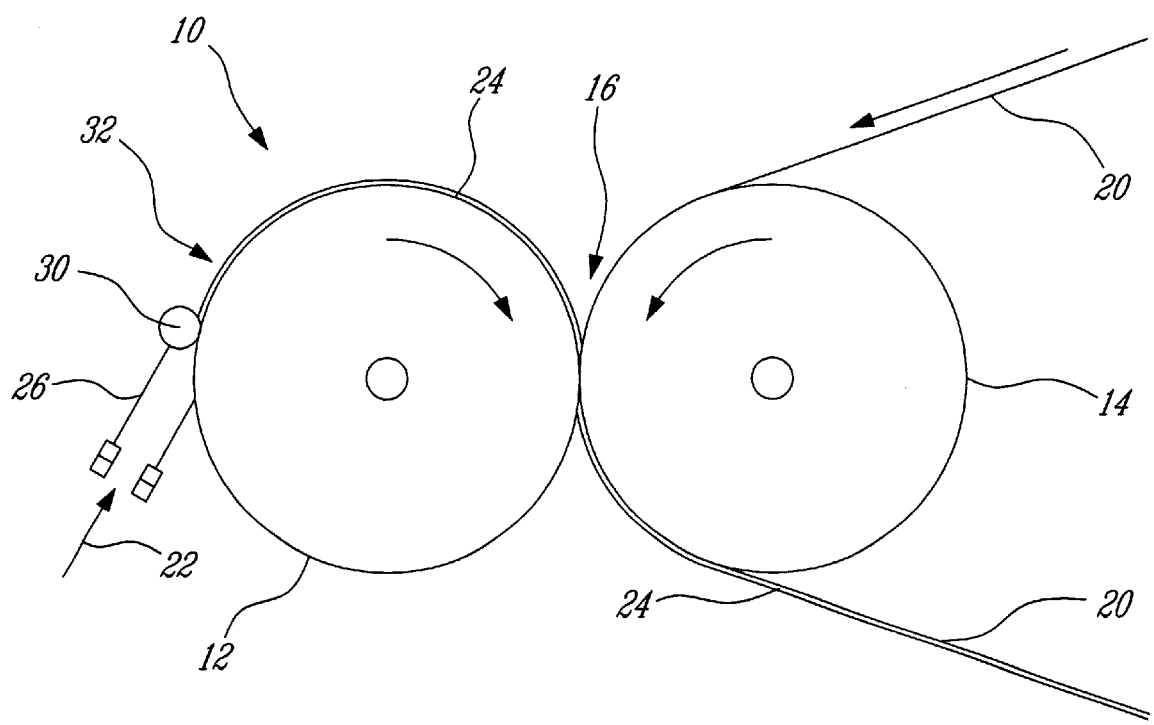
FIG. 1 is a schematic side view showing a typical film metering device as found in the prior art.

FIG. 2 shows a film metering device (10) incorporating a system according to a preferred embodiment of the present invention. This system comprises components installed directly in the film metering device (10). A first of these components is a small piezo-electric pressure transducer (40) that is flush-mounted on the outer cylindrical surface (34) of the metering rod (30), preferably at the center thereof. The pressure transducer (40) is embedded within the metering rod (30). A typical piezo-electric pressure transducer (40) suitable for this purpose would have a range of measurements from −50 kPa and 1400 kPa, relative to the atmospheric pressure, and a response time of 250 KHz or more. The diameter of such transducer (40) is generally in the order of 2,5 mm or less and the surface roughness is less than 3 $\mu$m, which minimizes the disturbances in the film (24). Other kinds of pressure transducers can also be used.

The piezo-electric pressure transducer (40) allows pressure measurements to be taken at one point at a time. These measurements are transmitted in the form of an analog signal P. The correlation between the signal P and the actual values of pressure is obtained from the results of a previous calibration procedure or from information supplied by the manufacturer of the pressure transducer (40). Measurements are repeated at a plurality of small intervals while the metering rod (30) is rotating the pressure transducer (40) through the metering nip. Alternatively, a plurality of successively-disposed pressure transducers can be provided. These intervals can be calculated as discrete time, angular values or any other equivalents. The goal is to at least obtain a pressure profile of the region in the metering nip (32). The metering rod (30) is preferably driven into rotation by means of an AC electric motor (not shown) for which a precise rotation speed can be imposed. The motor is designed to keep a constant rotation speed ($\omega$), which thus allows the rotation speed of the metering rod (30) to be known at all time. Nevertheless, a speed sensor (42) may be provided to known the rotation speed ($\omega$) of the metering rod (30).

FIG. 3 is a schematic representation of the flow pattern within the metering nip (32) between the transfer roll (12) and the metering rod (30). FIG. 4 is an example of a typical pressure profile and shows what is the pressure of the fluid on the surface (34) of the metering rod (30). This graph shows that there is a maximum pressure section near the minimum gap and a minimum pressure section thereafter.

The pressure profile is obtained by repeatedly sensing the pressure on the surface (34) of the metering rod (30). However, the system starts recording the signal P for obtaining a pressure profile when it reaches a threshold value corresponding to a pressure indicative of the beginning of the gap. This corresponds to position A in FIGS. 3 and 4. The pressure measurements are taken at predetermined time or angular intervals used as a referential system. For instance, the values of the rotation speed ($\omega$), the radius (R) of the metering rod (30) and the tangential speed ($V_m$) of the metering rod (30) may be used to calculate the relative circumferential distance between measurements. This allows to keep track of the position of the pressure transducer (40) relative to position A. The space between successive measurements should be small in order to obtain a suitable resolution of the pressure profile. The system continues to record the signal P throughout the metering nip (32) and until the pressure transducer (40) reaches the relative position D within the same revolution. The position D may be determined either by monitoring the signal P to determine the location where the pressure becomes stable, calculating the amount of time required to go from position A to position D or by an accurate position sensor, such as an optical sensor. The pressure measurements are preferably acquired for a number of successive rod revolutions, for example 10 revolutions. The data is then processed and filtered to obtain a mean profile from the 10 profiles. In the system illustrated in FIG. 2, the signal P is recorded in the memory of a computer (50). The pressure transducer (40) is connected to the computer (50) by means of a rotatable contact (44), which allows the interface between the rotatable metering rod (30) and the computer (50).

The torque applied on the metering rod (30) is measured by a torque sensor (60). The torque sensor (60) is connected to the metering rod (30), which means that the torque sensor (60) is able to measure the torque applied to the metering rod (30) by the driving motor (not shown). The torque sensor (60) may be mounted on the driving motor or an intermediary mechanical element and still be connected to the metering rod (30) within the meaning of the present invention.

The torque sensor (60) generates a signal T which is recorded by the computer (50). The signal T is indicative of the torque when the pressure profile is taken. The value of the torque may be an average value from a plurality of measurements or a value obtained from a single measurement. The correlation between the signal T and the actual value of the torque is obtained from the results of a previous calibration procedure or from information supplied by the manufacturer of the torque sensor (60).

Once all the data are in the memory of the computer (50), the maximum pressure value ($P_{max}$) and a minimum pressure value ($P_{min}$) are extracted or calculated from the resulting pressure profile. The respective relative positions ($X_{max}$, $X_{min}$) of these values are also determined. The computer (50) then calculates the value of the circumferential spacing (L) between the two positions ($X_{max}$, $X_{min}$), where $L = |X_{max} - X_{min}|$.

In the metering nip (32), the domain located between the two positions ($X_{max}$, $X_{min}$) s considered as if no flow recirculation occurs. For instance, a particle that enters through the position $X_{max}$ will exit through the position $X_{min}$. The flow is assumed to be laminar in the region and the inertia effects are not considered. This last assumption is considered acceptable in this context for a Reynolds number lower than 10. The Reynolds number is given by:

$$Re = \frac{\rho V_t W^2}{\mu L} \quad (1)$$

where ρ is he density of the fluid, W is the width of the film (24) and $\mu$ is the fluid viscosity.

The torque value (T) represents a global load applied on the whole metering rod (30). It has to be expressed rather as the tangential stress (T*) at the effective contact surface on the metering nip (32). This is given by the following expression:

$$T^* = \frac{T}{R \cdot W \cdot L} \quad (2)$$

where R is the radius of the metering rod (30).

FIG. 5 illustrates the velocity profile in the metering nip (32). The tangential stress can then be expressed as:

$$T^* = \frac{\mu V_t}{h_{app.}} \quad (3)$$

where $V_t$ is the tangential speed of the transfer roll (12) and $h_{app.}$ is an apparent thickness of a given fluid layer close to the metering rod (30), as defined in FIG. 5. The tangential speed ($V_t$) is calculated from the rotation speed of the transfer roll (12) and its radius. The rotation speed of the transfer roll (12) is obtained from a known preset value of the driving motor (not shown) or from measures taken by a corresponding sensor, such as the speed sensor (18) shown in FIG. 2.

The projection of the Stokes equation (3) in the x direction becomes:

$$\frac{\partial P}{\partial x} = \mu \frac{\partial^2 V_x}{\partial y^2} \quad (4)$$

Integrating once in the y direction gives:

$$\frac{\partial P}{\partial x} y = \mu \frac{\partial V_x}{\partial y} + K(x) \quad (5)$$

In order to apply this equation to the region, the approximated velocity profile, represented in FIG. 5, is considered. This leads to the following hypothesis:

$$\frac{\partial P}{\partial x} = \frac{P_{max} - P_{min}}{L}$$

The equation (5) then becomes:

$$\left(\frac{P_{max} - P_{min}}{L}\right) h_{app.} = \left(\frac{\Delta P}{L}\right) h_{app.} = \mu \frac{V_t}{h_{app.}} \quad (6)$$

Hence, equation (3) and (6) give:

$$h_{app} = \frac{T^*}{\left(\frac{\Delta P}{L}\right)} \quad (7)$$

The process viscosity ($\mu$) is preferably calculated using the following formula:

$$\mu = \frac{\left[\frac{T}{R * W * L}\right]^2}{\left[V_t * \left(\frac{P_{max} - P_{min}}{L}\right)\right]} \quad (8)$$

The apparent shear rate ($\dot{\gamma}$) can be expressed as:

$$\gamma = \frac{V_t}{h_{app}} \quad (9)$$

By combining equations (2), (7) and (9), it is possible to calculate the apparent shear rate ($\dot{\gamma}$) using the following formulae:

$$\gamma = \frac{\left[V_t * \left(\frac{P_{max} - P_{min}}{L}\right)\right]}{\left[\frac{T}{R * W * L}\right]} \quad (10)$$

The present invention is not limited to the described embodiment and encompasses any alternative embodiments within the limits defined by the claims.

What is claimed is:

1. A method for determining the process viscosity ($\mu$) of a fluid in a film metering device, the film metering device including a transfer roll, a metering rod and a metering nip in a space formed between the transfer roll and the metering rod, the metering rod having an outer cylindrical surface and being disposed parallel to the transfer roll, the method comprising the steps of:

obtaining a pressure profile of the fluid, representing the pressure of the fluid in the metering nip on the surface of the metering rod;

measuring a value of a torque (T) applied on the metering rod when the pressure profile is taken;

determining a maximum pressure value ($P_{max}$) and a minimum pressure value ($P_{min}$) from the pressure profile and respective positions ($X_{max}$, $X_{min}$) thereof;

determining a maximum a value of a circumferential spacing (L) between the position ($X_{max}$) of the maximum pressure value ($P_{max}$) and the position ($X_{min}$) of the minimum pressure value ($P_{min}$); and calculating the process viscosity ($\mu$) of the fluid using the values of the torque (T), the maximum pressure ($P_{max}$), the minimum pressure ($P_{min}$) and the circumferential spacing (L).

2. A method according to claim 1, wherein the process viscosity ($\mu$) is calculated according to the following formula:

$$\mu = \frac{\left[\frac{T}{R*W*L}\right]^2}{\left[V_t*\left(\frac{P_{max}-P_{min}}{L}\right)\right]}$$

where $V_t$ is a value of the tangential speed of the transfer roll, R is a value of the radius of the metering rod and W is a value of the width of a film formed on the transfer roll.

3. A method according to claim 2, further comprising the step of calculating the apparent shear rate ($\dot{\gamma}$) according to the following formula:

$$\gamma = \frac{\left[V_t*\left(\frac{P_{max}-P_{min}}{L}\right)\right]}{\left[\frac{T}{R*W*L}\right]}.$$

4. A method according to claim 2, wherein the step of obtaining a pressure profile includes:
(A) continuously sensing the pressure on the surface of the metering rod and generating a signal P indicative of a pressure value;
(B) beginning recording the signal P when it reaches a threshold value indicative of a beginning of the metering nip;
(C) keeping track of the position of the surface of the metering rod relative to a predetermined referential system at least from the beginning of the recording of the signal P; and
(D) continuing to record the signal P at a plurality of intervals until the pressure profile is obtained throughout the metering nip.

5. A method according to claim 4, wherein the step of obtaining a pressure profile includes:
repeating steps (B) to (D) for a plurality of revolution of the metering rod; and
calculating an average pressure profile from the plurality of pressure profiles.

6. A method according to claim 4, wherein the step of keeping track of the position of the surface of the metering rod relative to a predetermined referential system includes:
determining a value of a tangential speed ($V_m$) of the surface of the metering rod;
determining time intervals between each recorded signal P; and
calculating the relative position of each recorded signal P using the tangential speed ($V_m$) of the surface of the metering rod and the time intervals.

7. A method according to claim 2, wherein the step of measuring a value of the torque includes:
measuring the torque with a torque sensor and generating a signal T indicative of the torque; and
recording the signal T.

8. A system for determining the process viscosity ($\mu$) of a fluid supplied to a film metering device, the film metering device including a transfer roll and a metering rod, both defining between them a metering nip, the metering rod having an outer cylindrical surface and being disposed parallel to the transfer roll, the system comprising:
first means for obtaining a pressure profile of the fluid representing the pressure of the fluid in the metering nip on the surface of the metering rod;
second means for measuring a value of a torque (T) applied on the metering rod when the pressure profile is taken;
third means for determining a maximum value ($P_{max}$) and a minimum value ($P_{min}$) from the pressure profile and relative positions ($X_{max}$, $X_{min}$) thereof;
fourth means for determining the value of a circumferential spacing (L) between the position ($X_{max}$) of the maximum pressure ($P_{max}$) and the position ($X_{min}$) of the minimum pressure ($P_{min}$); and
fifth means for calculating the process viscosity ($\mu$) using the values of the torque (T), the maximum pressure value ($P_{max}$), the minimum pressure value ($P_{min}$) and the circumferential spacing (L).

9. A system according to claim 8, wherein the fifth means comprise means for calculating the process viscosity ($\mu$) according to the following formula:

$$\mu = \frac{\left[\frac{T}{R*W*L}\right]^2}{\left[V_t*\left(\frac{P_{max}-P_{min}}{L}\right)\right]}$$

where $V_t$ is a value of the tangential speed of the transfer roll, R is a value of the radius of the metering rod and W is a value of the width of a film formed on the transfer roll.

10. A system according to claim 9, further comprising means for calculating the apparent shear rate ($\dot{\gamma}$) of the fluid according to the following formula:

$$\gamma = \frac{\left[V_t*\left(\frac{P_{max}-P_{min}}{L}\right)\right]}{\left[\frac{T}{R*W*L}\right]}.$$

11. A system according to claim 9, wherein the first means include:
(A) sixth means for continuously sensing the pressure on the surface of the metering rod and generating a signal P indicative of a pressure value;
(B) seventh means for comparing the signal P to a threshold value indicative of a beginning of the metering nip;
(C) eighth means for keeping track of the position of the surface of the metering rod relative to a predetermined referential system; and
(D) ninth means for repeatedly recording the signal P.

12. A system according to claim 11, further comprising tenth means for calculating an average pressure profile from a plurality of pressure profiles.

13. A system according to claim 12, wherein the eighth means comprise:
means for determining a value of a tangential speed ($V_m$) of the surface of the metering rod;
means for determining time intervals between each recorded signal P; and means for calculating the relative position of each recorded signal P using the tangential speed ($V_m$) of the surface of the metering rod and the time intervals.

14. A system according to claim 9, wherein the second means comprise:
   means for measuring the torque (T) and generating a signal T indicative of the torque (T); and
   means for recording the signal T.

15. A system according to claim 14, wherein the means for measuring the torque (T) comprise a torque sensor connected to the metering rod.

16. A system according to claim 9, wherein the first means comprise a piezo-electric pressure transducer flush-mounted on the surface of the metering rod.

17. A system for determining the process viscosity ($\mu$) of a fluid supplied to a film metering device, the film metering device including a transfer roll and an adjacently-disposed metering rod, both forming between them a metering nip, the metering rod having a cylindrical outer surface and a rotation speed ($\omega$), the system comprising:
   a pressure sensor flush-mounted on the outer surface of the metering rod, the pressure sensor generating a first signal indicative of the pressure thereon;
   a torque sensor connected to the metering rod, the torque sensor generating a second signal (T) indicative of the torque applied on the metering rod; and
   a computer to record and process data, the computer calculating the process viscosity ($\mu$) based on the first signal (P), the second signal (T) and the rotation speed ($\omega$).

18. A system according to claim 17, wherein the process viscosity ($\mu$) is calculated according to the following formula:

$$\mu = \frac{\left[\frac{T}{R*W*L}\right]^2}{\left[V_t * \left(\frac{P_{max} - P_{min}}{L}\right)\right]}$$

where $V_t$ is a value of the tangential speed of the transfer roll, R is a value of the radius of the metering rod and W is a value of the width of the film on the transfer roll.

19. A system according to claim 18, wherein the computer further calculates the apparent shear rate ($\dot{\gamma}$) of the fluid according to the following formula:

$$\dot{\gamma} = \frac{\left[V_t * \left(\frac{P_{max} - P_{min}}{L}\right)\right]}{\left[\frac{T}{R*W*L}\right]}.$$

20. A system according to claim 18, wherein the pressure sensor comprises a piezo-electric pressure transducer.

* * * * *